United States Patent
Fezza

(10) Patent No.: US 9,504,605 B2
(45) Date of Patent: *Nov. 29, 2016

(54) LACRIMAL FILLER

(71) Applicant: FEZZA FAMILY PROPERTIES, LLC, Osprey, FL (US)

(72) Inventor: John P. Fezza, Osprey, FL (US)

(73) Assignee: Fezza Family Properties, LLC, Osprey, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/641,133

(22) Filed: Mar. 6, 2015

(65) Prior Publication Data

US 2015/0173951 A1  Jun. 25, 2015

Related U.S. Application Data

(63) Continuation of application No. 12/386,150, filed on Apr. 14, 2009, now Pat. No. 8,979,821.

(51) Int. Cl.
| | |
|---|---|
| *A61F 9/007* | (2006.01) |
| *A61L 24/08* | (2006.01) |
| *A61L 24/00* | (2006.01) |
| *A61K 47/36* | (2006.01) |

(Continued)

(52) U.S. Cl.
CPC ....... *A61F 9/00772* (2013.01); *A61B 17/1219* (2013.01); *A61B 17/12022* (2013.01); *A61B 17/12099* (2013.01); *A61B 17/12186* (2013.01); *A61K 9/0048* (2013.01); *A61K 47/36* (2013.01); *A61L 24/0015* (2013.01); *A61L 24/08* (2013.01); *A61B 2017/1205* (2013.01); *A61L 2400/06* (2013.01)

(58) Field of Classification Search
None
See application file for complete search history.

(56) References Cited

U.S. PATENT DOCUMENTS

| | | |
|---|---|---|
| 5,830,171 A | 11/1998 | Wallace |
| 5,840,054 A | 11/1998 | Hamano et al. |

(Continued)

FOREIGN PATENT DOCUMENTS

| | | |
|---|---|---|
| WO | WO2007/149832 A2 | 12/2007 |
| WO | WO2007/149832 A3 | 10/2008 |

OTHER PUBLICATIONS

"Form Fit® Intracanalicular Plug" brochure by Oasis Medical, Inc. (in 3 pages).

(Continued)

*Primary Examiner* — Ernst V Arnold
*Assistant Examiner* — Kyung Sook Chung
(74) *Attorney, Agent, or Firm* — Knobbe, Martens, Olson & Bear, LLP

(57) ABSTRACT

A biomaterial mass is inserted through a punctum into a canaliculus in the lacrimal outflow system with a syringe. The mass has an outer cross section that is less than the inner cross section of the canaliculus. The mass absorbs liquid to swell to form a lacrimal filler or sealing mechanism. The lacrimal filler has an external cross section that conforms to the internal cross section of the canaliculus and a soft outer surface relative to the surrounding tissues to prevent erosion of the canaliculus lining. The lacrimal filler forms an occlusion that prevents the outflow of liquid through the lacrimal outflow system to retain tears within the eye to maintain eye lubrication and wetness. The mass and syringe are provided in kit with a rubber stopper and, optionally, a punctal dilator, an injecting catheter, and an enzyme for dissolving or degrading the lacrimal filler at a later time.

16 Claims, 8 Drawing Sheets

(51) Int. Cl.
A61B 17/12 (2006.01)
A61K 9/00 (2006.01)

(56) References Cited

U.S. PATENT DOCUMENTS

| | | | |
|---|---|---|---|
| 6,016,806 | A | 1/2000 | Webb |
| 6,041,785 | A | 3/2000 | Webb |
| 6,234,175 | B1 | 5/2001 | Zhou et al. |
| 6,527,780 | B1 | 3/2003 | Wallace et al. |
| 8,979,821 | B2 | 3/2015 | Fezza |
| 2005/0095269 | A1 | 5/2005 | Ainpour et al. |
| 2005/0197614 | A1 | 9/2005 | Pritchard et al. |
| 2006/0040894 | A1 | 2/2006 | Hunter et al. |
| 2006/0074370 | A1 | 4/2006 | Zhou |
| 2007/0021762 | A1 | 1/2007 | Liu et al. |
| 2007/0259021 | A1 | 11/2007 | Friedlaender et al. |
| 2007/0298075 | A1 | 12/2007 | Borgia et al. |
| 2007/0299516 | A1 | 12/2007 | Cui et al. |
| 2008/0045911 | A1 | 2/2008 | Borgia et al. |

OTHER PUBLICATIONS

"Form Fit® Intracanalicular Plug" brochure by OASIS Medical, Inc. (2005) in 3 pages.
"OASIS Product Catalog" Table of Contents by OASIS Medical, Inc. (2005) in 2 pages.
"Hyaluronic Acid Review" downloaded from the website www.beautyproductscompared.com on Feb. 9, 2009 (in 2 pages).
"Odyssey's Loyalty Program" advertisement by Odyssey Medical of Bartlett, Tennessee (2008). (in 2 pages).
"Smart P!ug®" brochure by Medennium, Inc. (2007). (in 2 pages).
"Nourish Your Skin from the Inside Out with Hyaluronic Acid and Collagen" downloaded from the website www.smart-publications.com on Feb. 15, 2009. (in 5 pages).
"Ophthalmic Products" brochure by EagleVision, Enteroptyx, and Grace Medical of Memphis, Tennessee (in 4 pages).
"Re: What is Hyaluronic Acid" downloaded from the website www.madsci.org on Feb. 15, 2009 (in 2 pages).
Aragona, P., et al., "Sodium hyaluronate eye drops of different osmolarity for the treatment of dry eye in Sjogren's syndrome patients", Br. J. Ophthalmol 2002, 86(8) :879-84 (August) (in 6 pages).
Aragona, P., et al., "Long term treatment with sodium hyaluronate-containing artificial tears reduces ocular surface damage in patients with dry eye", Br. J. Ophthalmol 2002, 86(2): 181-4 (February) (in 4 pages).

Berry M, et al., "Hyaluronan in dry eye and contact lens wearers" by Adv. Exp. Med. Biol. 1998; 438: 785-90 (abstract only in 1 page).
Debbasch, C., et al "Cytoprotective effects of hyaluronic acid and Carbomer 934P in ocular surface epithelial cells", Invest. Opthalmol Vis. Sci. Nov. 2002 43 (11): 3409-15 (in 7 pages).
Final Office Action dated Jun. 7, 2011 in U.S. Appl. No. 12/386,150 in 11 pages.
Final Office Action dated May 12, 2014 in U.S. Appl. No. 12/386,150 in 16 pages.
Glaucoma Research Foundation (glaucoma.org/treatment/dry-eyes-and-glaucoma-double-trouble.php, last visit, Dec. 12, 2013). (in 2 pages).
Hamano, T., et al., "Sodium hyaluronate eyedrops enhance tear film stability", Jpn J. Opthalmol 1996; 40(1): 62-5 (abstract only in 2 pages).
Johnson, M.E., et al., "Carbomer and sodium hyaluronate eyedrops for moderate dry eye treatment", Optom. Vis. Sci. Aug. 2008: 85(8): 750-7 (abstract only in 2 pages).
Johnson, M.E., et al., "Effectiveness of sodium hyaluonate eyedrops in the treatment of dry eye". Graefes Arch Clin Exp Opthalmol. Jan. 2006 244 (1): 109-12 (E-Published Jun. 28, 2005) (abstract only in 2 pages).
Kenji Tomihata and Yoshito Okada, Preparation of Cross-linked Hyaluronic Acid Films of Low Water Content, 18 Biomaterials 189 (1997) (in 7 pages).
McDonald, C.C, et al. , "A randomized, crossover, multicentre study to compare the performance of .1% (w/v) sodium hyaluronate with 1.4% (w/v) polyvinyl alcohol in the alleviation of symptoms", Eye, Sep. 2002, 16(5): 601-7 (in 7 pages).
Norihiko, Y., et al., "Effectiveness of hyaluronan on corneal epithelial barrier function in dry eye" in Br. J. Opthalmol 1997, 81:533-536 (July) (Abstract). (in 3 pages).
Office Action dated Dec. 19, 2013 in U.S. Appl. No. 12/386,150 in 15 pages.
Office Action dated Feb. 2, 2011 in U.S. Appl. No. 12/386,150 in 10 pages.
Prabhasawat, P., "Performance profile of sodium hyaluronate in patients with lipid tear deficiency: randomized, double-blind, controlled, exploratory study", Br. J. Opthalmol. Jan. 2007 91 (1) : 47-50 (E-Published Sep. 14, 2006) (in 4 pages).
The Ocular Surface, "Management and therapy of dry eye", vol. 5, No. 2, (Apr. 2007). (in 16 pages).
Troiano, P., Monaco, G., "Effect of hypotonic .4% hyaluronic acid drops in dry eye patients: a cross-over study", Cornea, Dec. 27, 2008 (in 10 pages).

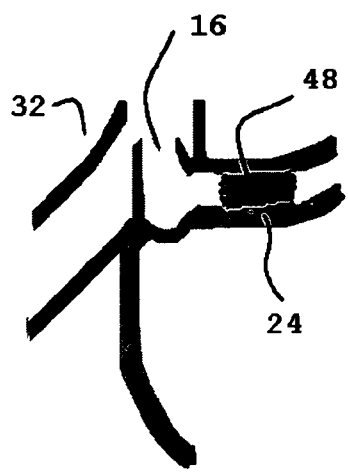
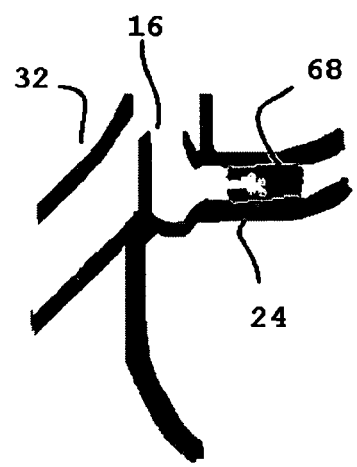
Fig. 10          Fig. 11
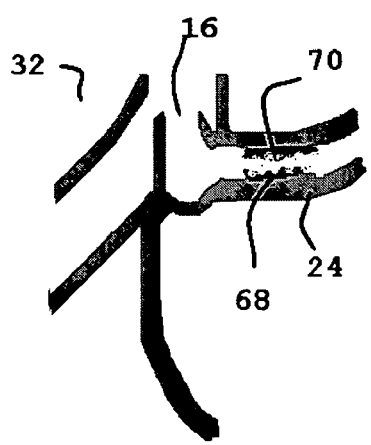
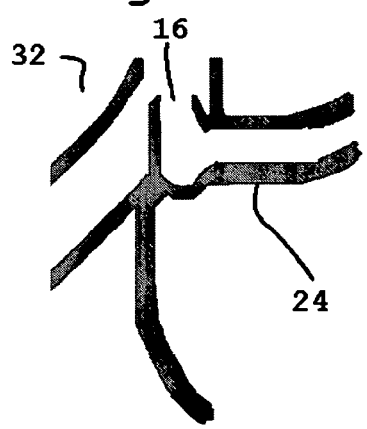
Fig. 12          Fig. 13
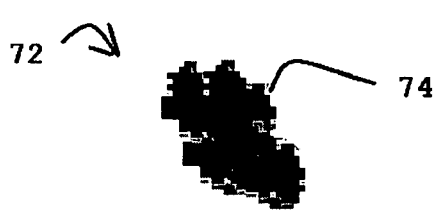
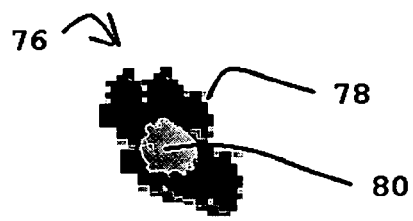
Fig. 14          Fig. 15

LACRIMAL FILLER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims the benefit under 35 U.S.C. §120 as a continuation of U.S. patent application Ser. No. 12/386,150 filed on Apr. 14, 2009, which is hereby incorporated by reference in its entirety.

BACKGROUND OF THE INVENTION

1. Field of the Invention

This invention relates to a lacrimal outflow system filler mechanism and, more particularly, to an apparatus, kit, and method for treating dry eyes by creating an occlusion in the lacrimal outflow system.

2. Description of the Related Art

Human tears include three basic components: (1) lipids; (2) an aqueous component; and (3) mucin. The absence of any one of these components causes discomfort in the eye. While tears are eliminated through various methods in the human eye, tear evaporation accounts for 20% or more of tear elimination within the tear film in adults.

A proper tear film is essential for maintaining eye health. Our eyes require moisture to wet and smooth the ocular surface to provide clear vision. Lacrimal secretions from the tear gland also protect the eye by washing away hazardous materials as well as providing important enzymes to fight infections. The pH for the tear film is maintained between 6.5 and 7.6.

The tear film is a complex structure composed of three layers: (1) an outer lipid layer; (2) a middle aqueous layer; and (3) an inner mucinous layer. The outer layer, produced by the Meibomian glands, prevents the tears from evaporating. The middle layer, produced by the lacrimal gland and accessory gland, wets the eye. The inner layer, produced by the conjunctival goblet cells, is responsible for spreading the tears out evenly. These three layers must be in a delicate balance to maintain a proper functioning tear film.

The human eye utilizes the lacrimal system to maintain the delicate balance of the tear film. The lacrimal system includes a lacrimal gland and a lacrimal tear duct. The lacrimal gland is analogous to a faucet within the lacrimal system. The lacrimal tear duct is analogous to a sink drain. The "faucet" works with the "drain" to maintain the balance within the tear film in the eye.

Hyaluronic acid (HA) is a natural, colorless, odorless gel that has various FDA approved, medical applications, including applications that relate to the tear film and to the eye in general. HA has been used for years by cataract surgeons. The surgeons inject the HA directly into the eye to maintain eyeball shape during surgery. HA is removed from eye through the use of an enzyme called hyaluronidase at the conclusion of surgery.

Many publications disclose applications for treating dry eyes using topical HA or HA solutions. The abstract entitled "Effectiveness of hyaluronan on corneal epithelial barrier function in dry eye" in Br. J. Ophthalmol 1997, 81: 533-536 (July) indicates that HA can be utilized as a lubricant to improve the corneal epithelial barrier function in eyes.

HA also has several medical uses that do not relate to the eye. The article entitled "Re: What is Hyaluronic Acid" downloaded from the website www.madsci.org on Feb. 15, 2009 discloses that HA is the major component of cartilage and joint lubrication. A publication entitled "Nourish Your Skin from the Inside Out with Hyaluronic Acid and Collagen" downloaded from the website www.smart-publications.com on Feb. 15, 2009 indicates that HA can be used a dietary supplement. A publication entitled "Hyaluronic Acid Review" downloaded from the website www.beautyproductscompared.com on Feb. 9, 2009 indicates that HA can be injected into the body.

Recently hyaluronic acid has been utilized as an injectable filler to fill wrinkles in the face. HA is a natural mucopolysaccharide that provides scaffolding for collagen in the body. HA is a repeating chain of simple sugars that are the same in all mammals and, therefore, are well tolerated and do not require testing for allergic reactions. They have a unique property of being osmotic, or swell and draw water with them. The amount of HA decreases as we age and, therefore, we lose its plumping and lubricating benefits.

Several applications that use HA to treat dry eyes have been disclosed. Dry eyes can be associated with the dysfunction of the lacrimal gland that causes it to supply insufficient moisture to the eyes. The resulting condition of dry eyes, commonly referred to as dry eye syndrome (DES), is heralded by a gritty, irritated ocular sensation as well as visual deterioration. DES can become so severe that corneal decomposition, ulceration and permanent visual loss can ensue. DES is a common condition that affects millions of people every year.

The tear film utilizes HA as a moisturizer and lubricant. Adding HA topically to tear replacement solution has been reported to be beneficial in treatment of dry eyes. Several publications have disclosed HA solutions that are used as eye lubricants, such as an abstract entitled "Effect of hypotonic 0.4% hyaluronic acid drops in dry eye patients: a cross-over study" by P. Troiano and G. Monaco, Cornea, 2008 Dec. 27 (10): 1126-30, an abstract entitled "Carbomer and sodium hyaluronate eyedrops for moderate dry eye treatment" by M.E. Johnson et al., Optom. Vis. Sci. 2008, Aug: 85(8): 750-7, an abstract entitled "Performance profile of sodium hyaluronate in patients with lipid tear deficiency: randomized, double-blind, controlled, exploratory study" by P. Prabhasawat, Br. J. Ophthalmol. 2007 January 91(1): 47-50 (E-Published Sep. 14, 2006), and an abstract entitled "Effectiveness of sodium hyaluronate eyedrops in the treatment of dry eye" by M. E. Johnson et al., Graefes Arch Clin Exp Ophthalmol. 2006 January 244(1): 109-12 (E-Published Jun. 28, 2005).

Several publications are directed to the use of HA as lubricants or eye drops include the abstract entitled "Cytoprotective effects of hyaluronic acid and Carbomer 934P in ocular surface epithelial cells" by C. Debbasch et al., Invest. Ophthalmol Vis. Sci. 2002 November 43(11): 3409-15, and the abstract entitled "A randomized, crossover, multicentre study to compare the performance of 0.1% (w/v) sodium hyaluronate with 1.4% (w/v) polyvinyl alcohol in the alleviation of symptoms" C. C. McDonald et al., Eye, 2002 September 16(5): 601-7, and the abstract entitled "Sodium hyaluronate eye drops of different osmolarity for the treatment of dry eye in Sjogren's syndrome patients" by P. Aragona et al., Br. J. Ophthalmol 2002, 86(8): 879-84 (August), "Hyaluronan in dry eye and contact lens wearers" by Berry M. Pastis et al., Adv. Exp. Med. Biol. 1998; 438: 785-90 (abstract unavailable), and the abstract entitled "Sodium hyaluronate eyedrops enhance tear film stability" by T. Hamano et al., Jpn J. Ophthalmol 1996; 40(1): 62-5. Publications that disclose the use of HA as an artificial tear substitute include the abstract entitled "Long term treatment with sodium hyaluronate-containing artificial tears reduces ocular surface damage in patients with dry eye" by P. Aragona et al., Br. J. Ophthalmol 2002, 86(2): 181-4 (February).

While these treatments may provide temporary relief to DES, these treatments are ineffective against many forms of DES. Keratitis sicca (or keratoconjunctivitis sicca) is the most common form of dry eyes. Some forms of keratitis sicca affect only the lacrimal gland and cause decreased tear production. Other forms affect the mouth by causing dry mouth.

Keratitis sicca occurs most commonly in women in the fifth and sixth decades. Symptoms include foreign body sensation, burning, irritation, pain and photophobia. Clinical signs include conjunctival injection giving rise to red eyes, and decreased tear film and corneal epithelial keratopathy on slit lamp exam.

The diagnosis of dry eyes and keratitis sicca is confirmed with decreased tear meniscus. The inferior tear meniscus height is normally 0.2 mm. A decreased tear film break-up (TFB) is another sign. TFB is defined by the time between the blink and the appearance of the first corneal dry spot appearing. A value less than 10 seconds is abnormal.

Another sign of DES is the staining of the cornea with flourescein or Rose Bengal. A Schirmer's test is often used to detect DES. A strip of filter paper is placed on the eye hanging over the lower lid to wick the tears. A measurement of less than 5 mm in 5 minutes can indicate a dry eye.

DES has a variety of causes but in general insufficient tears are produced to maintain an adequate aqueous layer. DES cannot be treated by merely stimulating the lacrimal gland to secrete more tears. Since it is not possible to increase lacrimal gland flow or turn the faucet higher, practitioners rely on adding moisture or blocking the outflow of tears away from the eye to create a wetter ocular environment.

A common type initial medical treatment for DES involves replacing moisture with artificial tears and ointment. One method involves adding wetting drops from artificial tear bottles to help reverse the dryness. Although artificial tears bring temporary relief, the manufactured solutions do not have the same composition as natural tears, so that the artificial tears are not as beneficial as a person's own tears.

Artificial tears have several other disadvantages. One disadvantage of artificial tears is the increased risk of allergies to preservatives within the artificial tears. This can be alleviated through the use of preservative-free tears for sensitive eyes.

Another disadvantage of artificial tears is that the relief tends to be short-lived. As a result, the treatment must be re-administered several times each hour, which is usually not practical.

Other treatments for dry eyes include night time lubrication with heavy ocular ointments, ocular moisture chambers, lid taping for improved closure, or eyelid surgery to aid in decreasing the open exposure of the eye.

The risk of DES also increases with increasing age. The application of drops by elderly patients can be challenging due to decreased dexterity, which represents another disadvantage of this approach.

Since we cannot increase tear production, an alternative approach involves slowing down the drainage of the tears through the lacrimal ducts by blocking the drain. The lacrimal outflow system is a series of tubes that serve to remove tears from the eye through the nose. Initially, tears drain from the eye through the upper and lower punctal openings, which lead into the canalicular canals, and ultimately to the lacrimal sac. It is in the lacrimal outflow system that drainage of tears from the eye can be adjusted.

Early attempts at sealing the puncta and/or the canalicular canals involved stitching the puncta shut, using electrical cauterization, or laser cauterization of the puncta and/or the canaliculus. Although these methods can provide an acceptable decrease in tear drainage, these methods may be difficult, painful, or irreversible without reconstructive surgery.

Sealing the tear ducts with cautery is painful and can be invasive and, potentially, irreversible. Since it is sometimes difficult to determine whether in a particular patient the drainage is too great or the tear production is too small, irreversible blockage is not desirable.

Punctal plugs or punctal occluders are solid silicone cylinders that are a popular method of first line treatment of DES. They act like a solid rubber cap in a sink drain. Such plugs or occluders have been disclosed by EagleVision, Enteroptyx, and Grace Medical of Memphis, Tenn., Odyssey Medical of Bartlett, Tenn., and Oasis Medical of Glendora, Calif.

Various punctum plugs have been disclosed by EagleVision, Enteroptyx, and Grace Medical of Memphis, Tenn. in their brochure entitled "Opthalmic Products." The plugs are the conventional silicone plugs with a tapered lower portion, a flanged upper portion, and a shaft-like connecting portion. The lower portion is inserted into the puncta. The connecting portion connects the lower portion to the upper portion.

A similar punctal plug has been disclosed by Odyssey Medical of Bartlett, Tenn. The plug includes the tapered lower portion, the flanged upper portion, and the shaft-like connecting portion.

U.S. Pat. No. 5,830,171 discloses a punctal occluder for blocking the flow of lacrimal fluid from the surface of an eye through a lacrimal punctum. The punctal occluder includes a shank having a distal end for insertion into the lacrimal punctum. The punctal occluder also includes a distal flange attached to the distal end of the shank for insertion into the lacrimal punctum. The distal flange includes a wing portion that has a first position extending substantially along the shank for allowing easy insertion of the distal flange into the lacrimal punctum. The distal flange also has a second position extending substantially outward from the shank for hindering unintentional removal of the distal flange from the lacrimal punctum.

U.S. Pat. No. 6,041,785 discloses a punctal plug that includes a proximal head, a distal body, and a shaft between the head and the body. The shaft of the plug is provided with one or more foldable portions, thereby permitting the length of the shaft to vary depending upon the degree to which the folds are folded or unfolded. In addition, the folds permit the wall of the shaft to easily bend, permitting the head and body of the plug to lie along different axes. As a result, the plug is shaped to accommodate both relatively long and short vertical puncta and the body of the plug may be angled relative to the head to accommodate a variety of anatomical structures.

U.S. Pat. No. 6,016,806 discloses a similar punctal plug that includes accordion-like folds to permit the thin wall of a shaft to easily bend. This permits the head and body of the plug to lie along different axes.

U.S. Pat. No. 6,234,175 discloses a punctal plug design and method for insertion which achieves a one-size-fits-all device for blocking the punctum or canaliculus of a patient. This is accomplished by using specifically defined materials having narrowly-defined glass transition temperature and/or melting temperature properties for fabricating the plug.

PCT Patent Publication No. WO2007/149832 discloses a punctal plug for the delivery of active agent to one or both of the tear fluid of the eye and to the nasolacrimal duct. The plug includes a body, a reservoir contained within the body, and a collarette. The reservoir has at least one opening and contains a polymeric material and at least one active agent.

U.S. Patent Publication No. 2007/0298075 discloses a punctal plug for the delivery of active agent to one or both of the tear fluid of the eye and to the nasolacrimal duct. The plug has a body, a reservoir contained within the body, and optionally a collarette. The reservoir has at least one opening and contains a polymeric material and at least one active agent.

U.S. Patent Publication No. 2007/0299516 discloses a punctal plug for the delivery of active agent to one or both of the tear fluid of the eye and to the nasolacrimal duct that comprise a body, at least one cap, and a collarette.

U.S. Patent Publication No. 2008/0045911 discloses punctal plugs for the delivery of active agents. The plugs have a body throughout which at least one active agent is dispersed or that is coated with a polymeric material containing at least one active agent.

U.S. Pat. No. 6,527,780 discloses a method for inserting punctal plugs into the lacrimal outflow system.

Another type of plug is disclosed in U.S. Patent Publication No. 2007/0021762. The ocular plug is formed from a biodegradable material. The plug includes a shaft and a cap. The ocular plugs are intended to occlude and repair discontinuities in the sclera, whether formed deliberately during injection or surgical foray into the eye or accidentally.

Many plugs are made from silicone and are placed painlessly into the puncta at the slit lamp. They act similar to placing a barrier over the drain of a sink that allows the sink to fill with water. The silicone plugs are popular and reimbursed by insurance for DES treatment.

A major problem with silicone plugs is that such plugs utilize a cap to hold the plug in place. The cap latches onto the eyelid surface, so that does not slip into the deeper tear duct. The cap may rub on the surface of the eye and irritate it.

The plug must be fitted for size due to the typical differences in tear duct dimension from patient to patient. As a result, obtaining the correct size plug can present a problem.

Another problem with silicone capped plugs is that they can become dislodged or lost. As a result, the benefits of such plugs are negated. The placement of such tiny plugs also presents a challenge.

U.S. Patent Publication No. 2006/0074370 discloses this type of "deeper" punctal plug. The punctal plug is made from an acrylate polymer or copolymer in the form of a solid rod that changes shape with the temperature change that occurs upon insertion into a canaliculus within the lacrimal outflow system. Once inside the canaliculus, the rod absorbs liquid to swell to its original cross section. These types of plugs are commonly referred to as intracanalicular plugs.

Intracanalicular plugs have several disadvantages. The hardened intracanalicular plug can erode in the soft inner wall of the canallculus, which causes granulation tissue and infection. This requires surgical removal.

Similar plugs have been disclosed by Oasis Medical of Glendora, Calif., and Medennium, Inc. of Irvine, Calif. The Oasis Medical plug is sold under the trademark Form Fit®. The Medennium plug is sold under the trademark Smart Plug®.

Other approaches involve different materials or surgical procedures. Temporary collagen plugs that sit below the puncta are also available. However, such plugs only last for about one week.

The principal theory of blocking the outflow of tears is fundamentally sound, as it involves using the patient's own tears to lubricate the eyes. The current types of tear plugs all have their unique set of problems as listed above. Therefore, there is need for a plug that is easy to place, effectively blocks the outflow of tears, comfortable, long lasting, easily reversible, and has a low potential for infection.

SUMMARY OF THE INVENTION

In accordance with the present invention there is provided an apparatus for treating dry eyes that includes a biomaterial mass inserted into a canaliculus in the lacrimal outflow system having an outer cross section less than the inner cross section of the canaliculus. The biomaterial mass absorbs liquid within the canaliculus to swell to form a lacrimal filler to seal the canaliculus at least partially. The lacrimal filler has an external cross section conforming to the internal cross section of the canaliculus and a soft outer surface relative to the surrounding tissues to prevent erosion of the canaliculus lining. The lacrimal filler forms an occlusion to prevent the outflow of liquid through the lacrimal outflow system to retain tears within the eye to maintain eye lubrication and wetness.

Further in accordance with the present invention, there is provided a kit for treating dry eyes that includes a syringe and a biomaterial mass. The syringe injects the biomaterial mass into a canaliculus in the lacrimal outflow system to absorb liquid within the canaliculus and swell to conform the outer surface of the mass to the inner surface of the canaliculus to form a sealing mechanism for sealing the canaliculus at least partially. The sealing mechanism outer surface is sufficiently soft relative to the inner surface of the canaliculus to prevent the sealing mechanism outer surface from eroding the canaliculus lining. The sealing mechanism forms an occlusion to prevent the outflow of liquid through the lacrimal outflow system to retain tears within the eye to maintain eye lubrication and wetness.

Further in accordance with the present invention, there is provided a method for treating dry eyes that includes the step of inserting a biomaterial mass into a canaliculus in the lacrimal outflow system. Liquid is absorbed with the biomaterial mass in the canaliculus to swell to form a soft seal within the canaliculus that does not erode the inner lining of the canaliculus. The canaliculus is sealed with the soft seal at least partially. The outflow of liquid through the lacrimal outflow system is prevented with the soft seal to retain tears within the eye to maintain eye lubrication and wetness.

Accordingly, a principal object of the present invention is to provide a treatment for dry eye syndrome.

Another object of the present invention is to provide a lacrimal filler to retain tears to treat dry eye syndrome.

Another object of the present invention is to provide a seal or sealing mechanism for preventing the flow of tears through the lacrimal outflow system.

A further object of the present invention is to provide a treatment for improving eye lubrication and wetness.

These and other objects of the present invention will be more completely described and disclosed in the following specification, accompanying drawings, and appended claims.

BRIEF DESCRIPTION OF THE DRAWINGS

FIG. 10 is a schematic view in side elevation of the initial dissolution of a lacrimal filler with an enzyme.

FIG. 11 is a schematic view in side elevation of the dissolution of the lacrimal filler shown in FIG. 10 after a predetermined period of time.

FIG. 12 is a schematic view in side elevation of the lacrimal filler shown in FIG. 11 after a sufficient amount of filler material has been dissolved to allow tears to flow through the lacrimal outflow system.

FIG. 13 is a schematic view in side elevation of the lower canaliculus shown in FIGS. 10-12 after the lacrimal filler has been essentially dissolved.

FIG. 14 is a schematic illustration of another embodiment of the lacrimal filler that includes a drug for delivery within the lacrimal system or the surrounding tissues.

FIG. 15 is a schematic illustration of another embodiment of the lacrimal filler that includes an inner core for holding a drug for delivery within the lacrimal system or the surrounding tissues.

DESCRIPTION OF THE PREFERRED EMBODIMENTS

Figure 1:
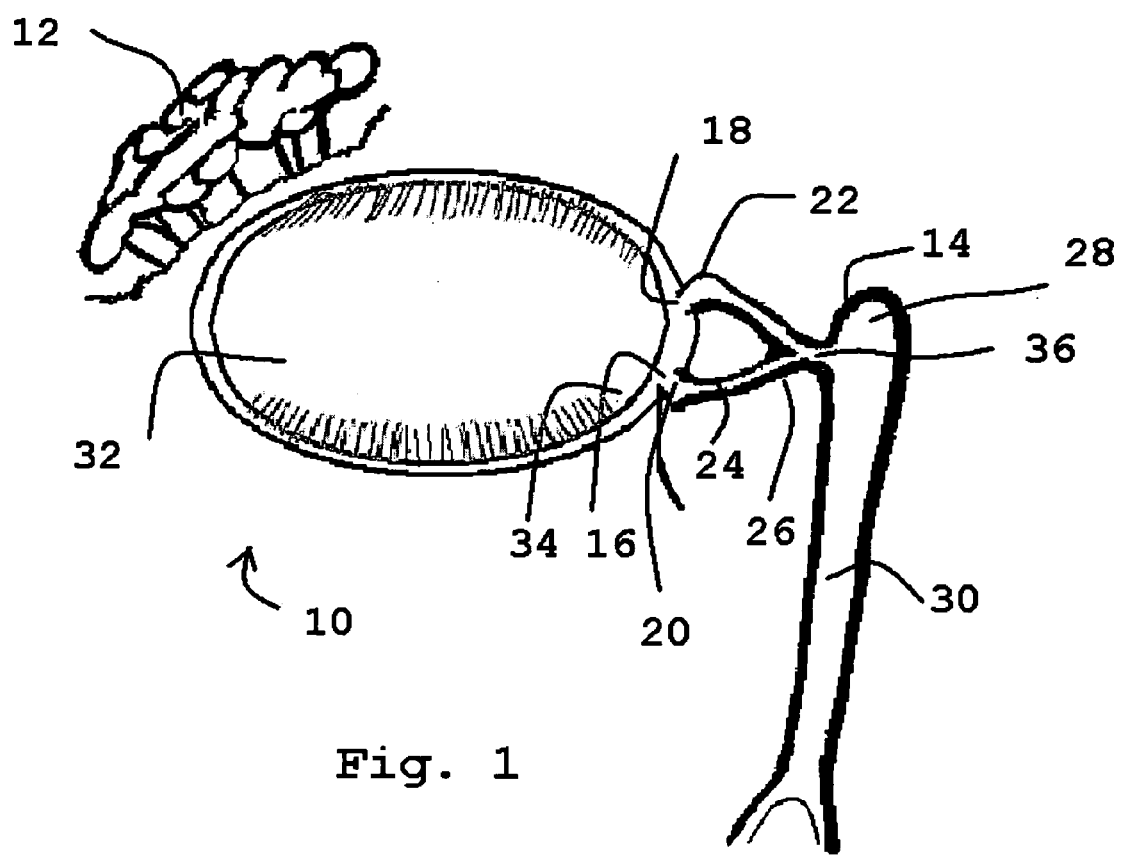
FIG. 1 is a fragmentary view in side elevation of the lacrimal system.

Referring to the drawings and, particularly, to FIG. 1, there is illustrated the human lacrimal system generally designated by the numeral 10. The lacrimal system 10 is divided into the secretory component or the lacrimal gland 12 and the excretory components that make up the lacrimal outflow system 14. The lacrimal outflow system 14 includes the puncta 16 and 18, the ampulla 20, the upper canaliculus 22, the lower canaliculus 24, common canaliculus 26, lacrimal sac 28, and nasolacrimal duct 30.

The eye 32 is positioned between the lacrimal gland 12 and the lacrimal outflow system 14. The eye 32 includes the medial canthal area 34. Tears pool within the medial canthal area 34 and enter the puncta 16, 18 to be eliminated through the lacrimal sac 28 into the nose (not shown).

The puncta 16, 18 are small orifices on the upper and lower lid margins, measuring 0.5-1.5 mm in diameter. The vertical ampulla 20 is typically 2 mm in length.

The canaliculi 22, 24 are essentially cylindrical tubes that dilate up to 2 mm in diameter. They are lined by stratified, nonkeratinized squamous epithelium, as is the lacrimal sac 28. The canaliculi 22, 24 are each typically 8-12 mm long. The canaliculi 22, 24 join to form the single common canaliculus 26 that connects to the lacrimal sac 28.

The common canaliculus 26 communicates with the lacrimal sac 28 to form the Valve of Rosenmueller 36. The Valve of Rosenmueller 36 is a fold of mucosa at the lateral tear sac wall, acting as a valve to prevent regurgitation of tears from the sac back into the canaliculus 22, 24.

The typical lacrimal sac 28 is 12-15 mm long. The typical nasolacrimal duct 30 is 12-18 mm long. The nasolacrimal duct 30 empties under the inferior meatus (not shown) to eliminate tears under the inferior turbinate of the nose (not shown). The lacrimal system 10 typically handles as much of 14-18 ul/min of tears.

Figure 2:
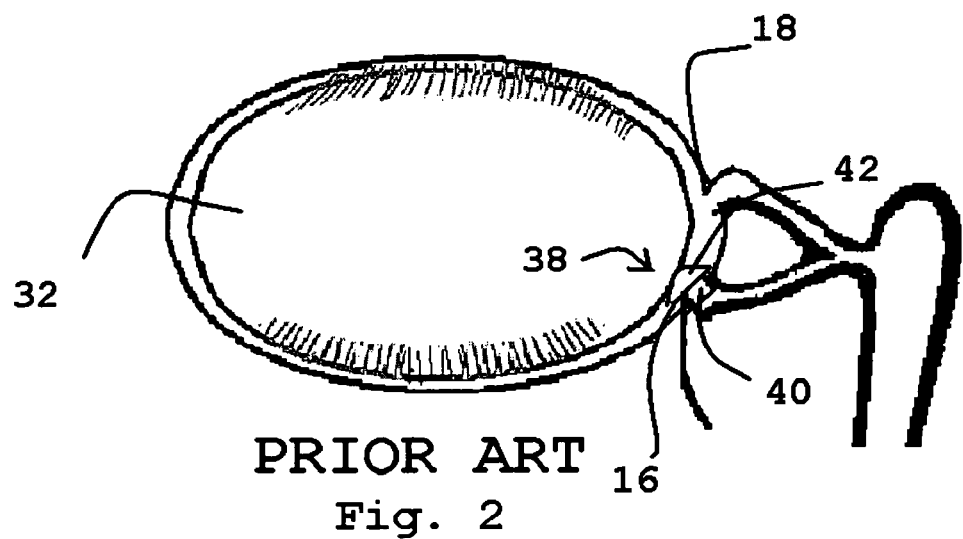
FIG. 2 is a fragmentary view in side elevation of a prior art punctal plug within the lacrimal outflow system.
Figure 3:
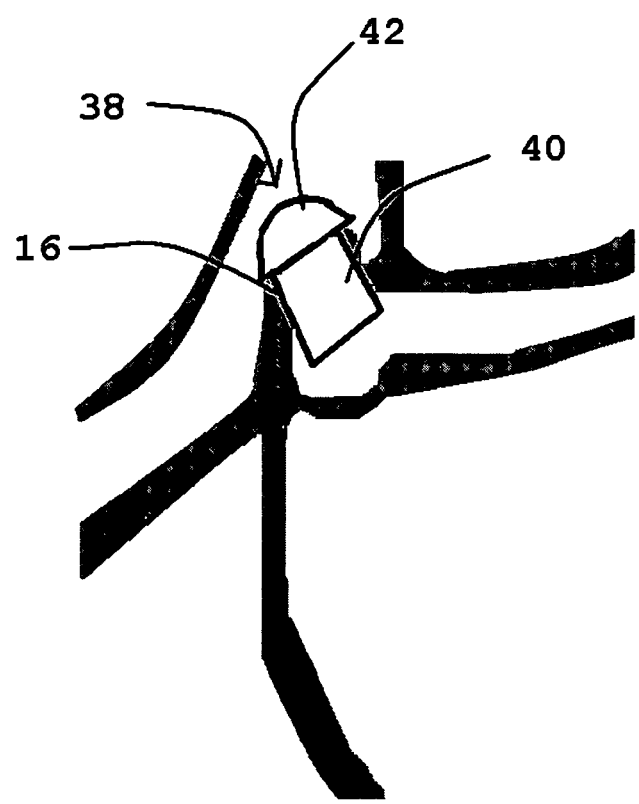
FIG. 3 is an enlarged schematic view in side elevation of the punctal plug shown in FIG. 2.

Referring now to FIGS. 2-3, there is illustrated a conventional punctal plug generally designated with the numeral 38 for treating dry eye syndrome. The plug 38 is positioned in the puncta 16, 18 to stop the egress of tears from the eye 32. The punctal plug 38 allows the tears to stay on the surface of the eye 32 longer. The punctal plug 38 also allows the tears to bath the eye 32 with lubrication.

The punctal plug 38 includes an essentially cylindrical body 40, an upper flange portion 42, and optionally, a tapered portion (not shown) that extends from the cylindrical body 40. The flange portion 42 forms a cap having a cross section that is greater than the cross section of the puncta 16, 18 to prevent the plug 38 from sliding through the puncta 16, 18 and into the lacrimal outflow system 14.

The plug 38 is typically made from silicone or acrylic materials. The plug 38 is formed from solid, bulk materials through conventional fabricating or molding techniques. The plug 38 is integral or formed from multiple solid, bulk materials, so that the plug 38 remains essentially intact within the puncta 16, 18 throughout its useful lifetime and after extraction from the canaliculi 22, 24.

The plug 38 acts as a cap or plug within a drain of a sink. The plug 38 allows the eye 32 to fill with tears but has the typical problems that are associated with conventional punctal plugs that are described above.

Figure 4:
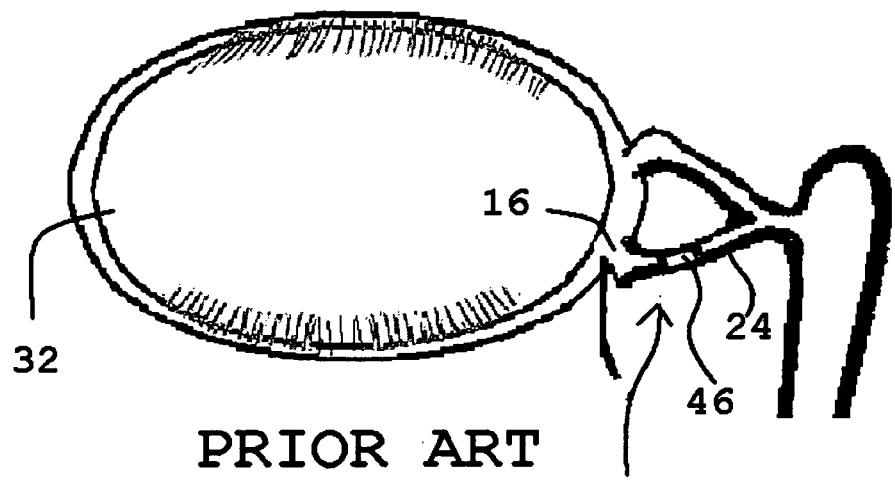
FIG. 4 is a fragmentary view in side elevation of a prior art intracanalicular plug within the lacrimal outflow system.
Figure 5:
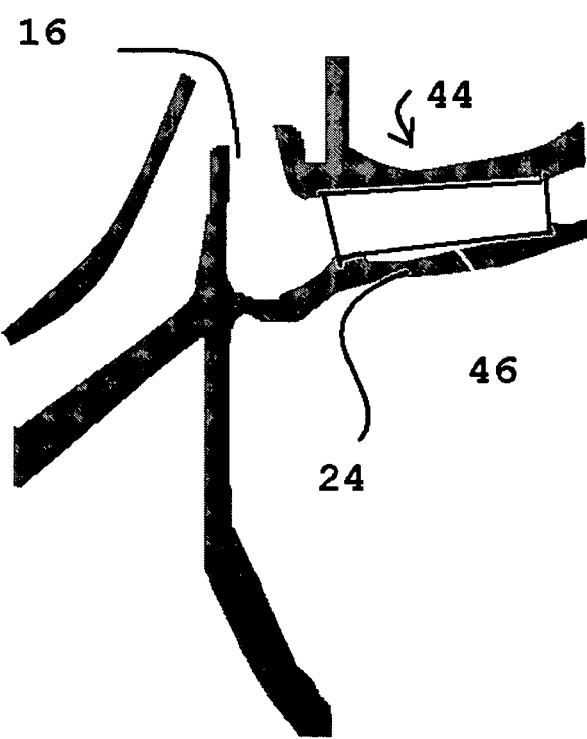
FIG. 5 is an enlarged schematic view in side elevation of the intracanalicular plug shown in FIG. 4.

Referring now to FIGS. 4-5, there is illustrated a conventional deeper, canalicular plug 44. Unlike the plug 38 shown in FIGS. 2-3, the plug 44 does not include an upper flange portion 42. Rather, the plug 44 includes an essentially cylindrical body 46 that is set within a canaliculus 24 in the lacrimal outflow system 14.

The plug 44 is placed below the surface of the eye lid, so that it does not rub on the eye 32 or fall out. The canalicular plug 46 is made from an acrylic material that is placed into the lower lid and changes shape by shrinking and hardening in place through a thermoplastic reaction. The burrowing of the hardened plug 44 creates a significant risk of infection in many patients because the rough outer surface of the plug 44 erodes the smooth lining of the canaliculus 24.

Often, the intercanalicular plug 46 cannot be removed by simple irrigation or flushing, as suggested.

The plug 44 causes a proliferation of beefy tissue called granulation tissue, which is a reaction to a foreign body. Bacteria may become entrapped deeper into the lacrimal outflow system 14, so that infection may occur or surgical removal may become necessary.

Similar to the plug 38 shown in FIGS. 2-3, the plug 44 is formed from solid, bulk materials through conventional fabricating or molding techniques. In one embodiment the plug 44 is an integral, solid bulk material. In another embodiment the plug 44 is formed from multiple solid bulk materials, so that the plug 44 remains essentially intact within the canaliculus 24 throughout its useful lifetime. The plug 44 also remains intact after it is extracted from the canaliculi 22, 24.

While the prior art plug 44 is intended to conform to the walls of the tear duct, the inherent rigidity of the bulk material prevents the plug 44 from conforming to the surface of the canaliculus 24 in a comfortable, non-damaging manner. Often, a lacrimal flush or multiple lacrimal flushes are required to remove the plug 44 from the canaliculi 22, 24. However, such flushes are often unsuccessful. Also, it is difficult to monitor the status of the plug 44 below the surface of the skin.

Referring now to FIGS. 6-10, there is shown in accordance with the present invention a punctal occluder generally designated by the numeral 48. The punctal occluder 48 is a lacrimal filler for treating dry eyes in suitable subjects, including mammals and, in particular, humans. The lacrimal filler 48 is used to treat dry eye syndrome by preventing tears that are produced in the secretory portion 12 of the lacrimal system 10 shown in FIG. 1 from flowing through the excretory portion 14 of the lacrimal system 10.

The lacrimal filler 48 forms an occlusion or sealing mechanism that prevents the outflow of liquid through the lacrimal outflow system 14 within the lower canaliculus 24. The lacrimal filler 48 retains tears within the eye 32 to maintain eye lubrication and wetness.

Figure 6:
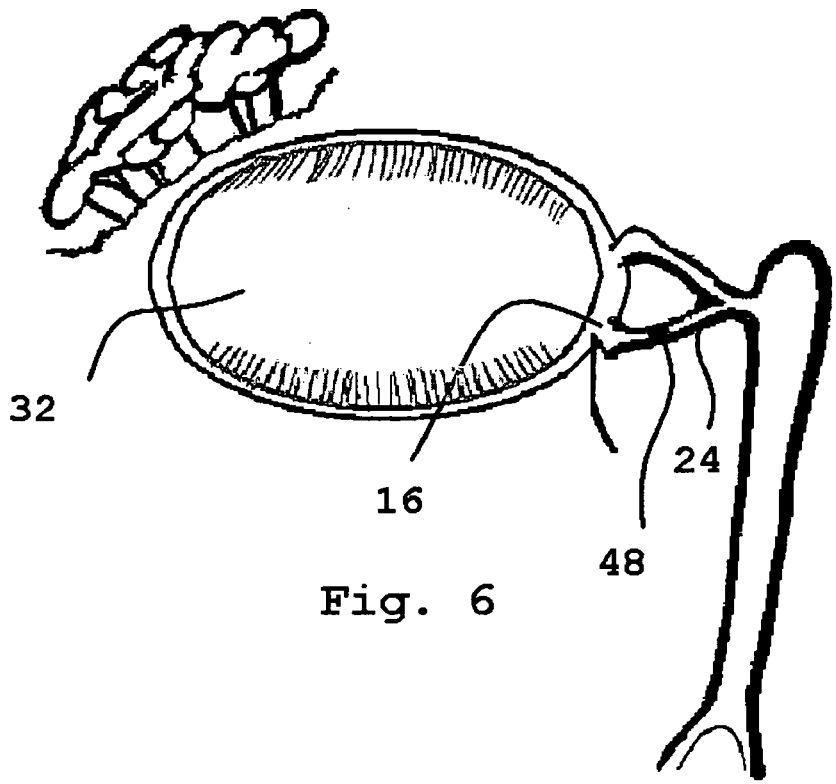
FIG. 6 is a fragmentary view in side elevation of a lacrimal filler in accordance with the present invention within a lower canaliculus of the lacrimal outflow system.
Figure 7:
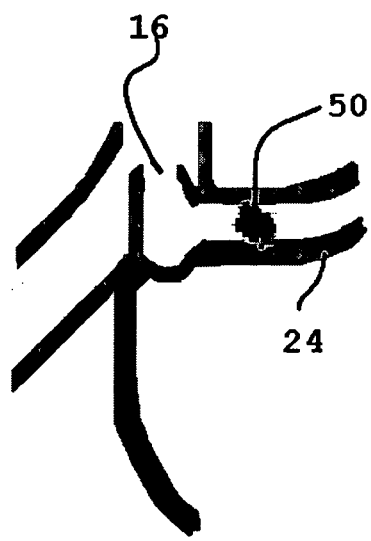
FIG. 7 is an enlarged schematic view in side elevation of a canaliculus into which a biomaterial mass has been injected.

As shown in FIGS. 6-7, the lacrimal filler 48 is formed from a biomaterial mass 50 inserted into the canaliculus 24. The mass 50 has an outer cross section that is less than the inner cross section of the canaliculus 24. The mass 50 absorbs liquid within the canaliculus 24 to swell to form the lacrimal filler 50 to at least partially seal the canaliculus 24. The lacrimal filler 50 sits in the canaliculus 24 below the lid margin and does not rub on the lid to irritate the eye 32.

Unlike the prior art plugs 38, 44 shown in FIGS. 2-5, the lacrimal filler 48 is not formed from a solid, bulk material. Rather, the lacrimal filler 48 is formed from a suitable, viscous biomaterial mass of material for forming occlusions in the canaliculi 22, 24 of the lacrimal outflow system 14 shown in FIG. 1. Preferably, the viscous biomaterial mass is delivered with a liquid component that has the ability to lubricate the eye 32.

Suitable, viscous biomaterials include any suspension or agglomeration of particles that form an occlusion in the lacrimal outflow system 14. Suitable materials also include, but are not necessarily limited to, colloidal systems, colloidal dispersions, colloidal suspensions, emulsions, latices, sols and gels. Preferably, the mass 50 is formed from polysaccharides, such as glycosaminoglycans and, particularly, hyaluronic acid. Hyaluronic acid has the ability to lubricate the eye 32.

Figure 8:
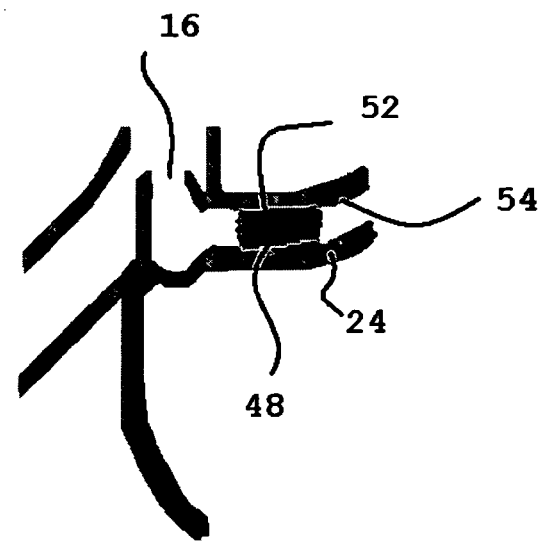
FIG. 8 is a view similar to FIG. 7, illustrating the lacrimal filler formed from the biomaterial mass within the canaliculus.

As illustrated in FIG. 8, the lacrimal filler 48 has an external cross section that conforms to the internal cross section of the canaliculus 24. The lacrimal filler 48 has a soft outer surface 52 relative to the surrounding tissues to prevent erosion of the canaliculus lining 54. Preferably, the lacrimal filler 48 is made from hyaluronic acid.

Hyaluronic acid, as a biomaterial mass in the present invention, is useful for blocking the outflow of tears and for lubricating the eye 32. Hyaluronic acid is hydrophilic and binds with water to cause swelling. As shown in FIG. 8, the hyaluronic acid upon injection into the canaliculus 24 absorbs liquid to mold gently into place without abrading the canaliculus interior surface 54 or forming rough edges thereon. The hyaluronic acid mass 50 conforms to the interior of the canaliculus 24 to form an occlusion 48 inside the lacrimal outflow system 14 shown in FIGS. 6 and 8.

Hyaluronic acid for use in the biomaterial mass 50 is available in several forms. Suitable forms include hyaluronic acid crystals, hyaluronic acid crystals suspended in hyaluronic acid liquid, hyaluronic acid gel, hyaluronic acid gel particles with hyaluronic acid solid particles, and hyaluronic acid solid particles. The hyaluronic acid gel particles are injected into the canaliculus as a pure gel without solid particles. Alternatively, hyaluronic acid solid particles are injected without any fluid component depending on the patient needs.

One suitable form of hyaluronic acid includes small hyaluronic acid crystals carried in a liquid hyaluronic acid continuous phase. The liquid hyaluronic acid phase acts as delivery vehicle or river to transport the small solid gel hyaluronic acid particles.

In operation as shown in FIG. 8, the solid gel hyaluronic acid particles swell until constrained by the inner surface 54 of the canaliculus 24. Once the swollen particles conform to the surface 54, the particles form an occlusion within the canaliculus 24 to retain tears within the eye 32. These occlusions typically last more than one year.

Figure 9:
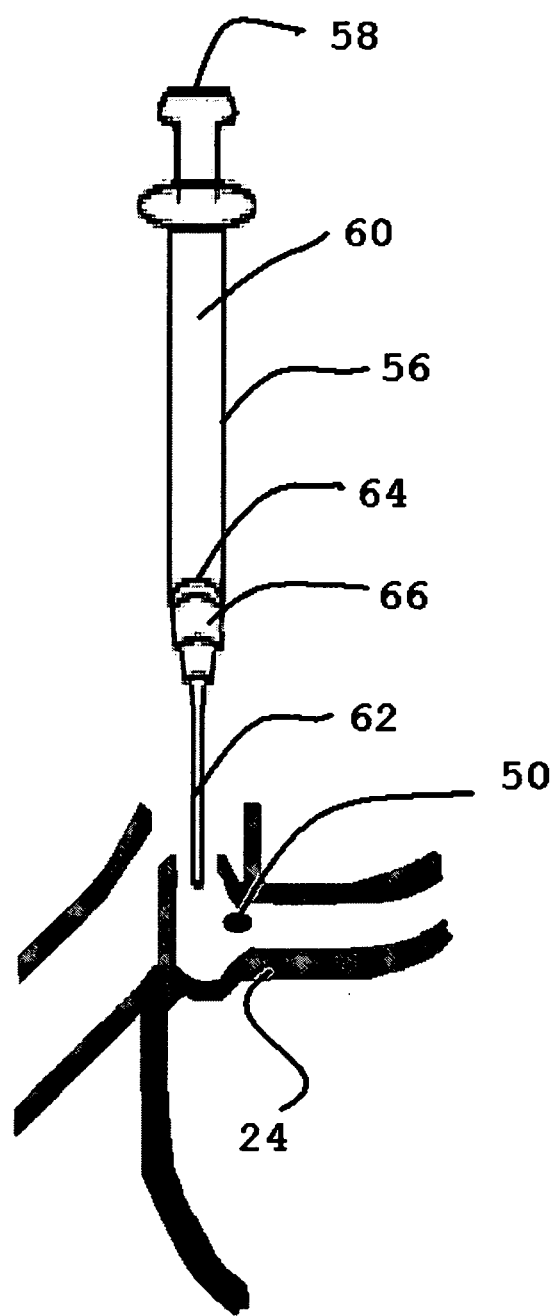
FIG. 9 is a schematic view in side elevation illustrating the injection of the biomaterial mass to form the lacrimal filler within the lower canaliculus.

In accordance with the present invention, various concentrations of hyaluronic acid are available for forming the biomaterial mass 50. The mass 50 is formed from a solution of hyaluronic acid that has a suitable concentration, including concentrations of less than 1 mg/ml and greater than 100 mg/ml prior to insertion into the canaliculus 24, as shown in FIG. 9. Preferably, the solution has a hyaluronic acid concentration of between 1 mg/ml and 100 mg/ml, between 15 mg/ml and 25 mg/ml, or about 22 mg/ml prior to insertion into the canaliculus 24.

Suitable forms of hyaluronic acid include hyaluronic acid with varying degrees of crosslinking, ranging from 0% to 100% crosslinking The degree of crosslinking is the number of crosslinks between the individual crosslinked hyaluronic acid chains. Greater degrees of crosslinking create a firmer more solid hyaluronic acid product or at least a highly viscous product. Preferably, a significant portion of the hyaluronic acid has a degree of crosslinking of at least 10% or from 60% to 95% crosslinking to produce firm gel particles.

Referring to FIG. 9, there is illustrated a method for inserting the biomaterial mass 50 into a canaliculus 24. The mass 50 is injected into the canaliculus 24 with a lacrimal injector or syringe 56. Preferably, a lacrimal punctal dilator (not shown) is inserted into the punctum 16 and stretches the punctum 16 to facilitate insertion of the syringe 56 and a catheter (not shown) into the canaliculus 24.

After the mass 50 is injected, as shown in FIG. 7, the mass 50 absorbs liquid to swell to form the soft seal or lacrimal filler 48, as shown in FIG. 8 within the canaliculus 24. The mass 50 forms the lacrimal filler or soft seal 48 to seal the canaliculus at least partially. The lacrimal filler 48 prevents the outflow of liquid through the lacrimal outflow system 14 to retain tears within the eye to maintain eye lubrication and wetness.

As shown in FIG. 9, the placement of the hyaluronic acid mass 50 is achieved painlessly with a lacrimal injector 56, which is similar to conventional lacrimal irrigators. The prepackaged syringe 56 includes a plunger 58, a cylindrical syringe chamber 60, and a tip 62. The cylindrical syringe chamber 60 includes a threaded portion 64 that connects to an upper portion of the tip 66. Preferably, the tip 62 is a metal lacrimal injector.

Initially, the chamber 60 includes a rubber stopper (not shown) that is connected to the threaded portion 64. Prior to insertion into the puncta 16, the rubber stopper is removed and replaced with the tip 62.

The hyaluronic acid mass 50 is packaged within the syringe cylindrical chamber 60. Preferably, the hyaluronic acid mass 50 is prepackaged in a clean or sterile manner in individual single use syringes with a rubber cap (not shown). Preferably, the syringe 56 includes from 0.1 cc to 1 cc or typically about 0.25 cc of hyaluronic acid per syringe.

In operation, a doctor removes the disposable rubber cap (not shown) and places the metal lacrimal irrigator 62 on the syringe 56 to deliver the hyaluronic acid mass 50. Optionally, the doctor places a numbing drop or anesthetic (not shown) into the eye 32. The next step involves inserting the punctal dilator (not shown) into the puncta 16 to stretch the puncta 16 and canaliculus 24. Thereafter the mass 50 is injected into the canaliculus 24. The catheter (not shown) and the syringe 56 are withdrawn, while the viscous mass 50 is deposited in the canaliculus 24 to form the lacrimal filler 48 shown in FIG. 6.

As shown in FIG. 9, the placement of the mass 50 does not require painful injection with a needle. Rather, the lacrimal irrigator 62 is inserted through the intact puncta 16 and advanced into the canaliculus 24 in a gentle, simple manner. The procedure is performed in a doctor's office or in any other similar environment. The procedure has the advantage that it is a similar procedure as irrigating a tear duct.

Typically, the procedure takes less than five minutes. The syringe 62 is discarded as medical waste. The patient returns in two weeks for reassessment. The mass 50 expands with water absorption from the position shown in FIG. 7 to the position shown in FIG. 8 to conform and fill the canaliculus 24, so that the tears do not leak around the soft seal to minimize complications. The procedure is quick, painless and effective.

The prepackaged syringes are sold as part of a kit for treating dry eye syndrome. Optionally, the kit includes the lacrimal catheter (not shown) and punctal dilator (not shown). The packaging of the syringe 56 and the mass 50 is similar to the packaging of facial fillers.

Referring now to FIGS. 10-13, there is illustrated a method for reversing the dry eye treatment in accordance with the present invention. The method includes dissolving the lacrimal filler 48 with a suitable enzyme. Suitable enzymes include any enzyme that dissolves or degrades the material that forms the lacrimal filler 48. Preferably, the enzyme dissolves or degrades the material almost instantaneously.

With the mass 50 forming the filler 48 as shown in FIG. 10, the enzyme is inserted into the canaliculus 24 with a lacrimal catheter (not shown) and syringe (not shown) in a manner similar to the insertion of the mass 50. The enzyme is inserted until it flows through the punctum 16 into the canaliculus 24. Within the canaliculus 24, the enzyme contacts the surface of the lacrimal filler 48 to begin dissolving or degrading the material that forms the lacrimal filler 48.

As shown in FIG. 11 the enzyme begins to dissolve the lacrimal filler 68 until a channel 70 is formed, as shown in FIG. 12. The channel 70 allows tears to flow from the eye 32 through the punctum 16 and the canaliculus 24 and out of the lacrimal outflow system 14 shown in FIG. 1.

As shown in FIG. 13, the enzyme continues to dissolve the lacrimal filler material until the canaliculus 24 is completely clear. As a result, the method for treating dry eyes shown in FIGS. 6-9 is completely reversible.

The selection of an enzyme is not critical, provided that the enzyme has the ability to dissolve or degrade the lacrimal filler material. Hyaluronic acid degrades by the enzyme hyaluronidase, which routinely used in eye surgery in which hyaluronic acid is used. Hyaluronidase removes hyaluronic acid essentially instantaneously. Both hyaluronic acid and hyaluronidase are FDA approved compounds in eye and skin procedures.

Referring now to FIG. 14, there is schematically illustrated another embodiment of the lacrimal filler generally designated by the numeral 72. Unlike the embodiments shown in FIGS. 6-13, the lacrimal filler 72 shown in FIG. 14 includes a mass 74 of material that is specially adapted for the delivery of medications. A benefit of using a mass 74 that is adapted for drug delivery is that the medications or drugs are released to the ocular surface as the lacrimal filler 72 dissolves.

The drug embedded within the mass 74 includes any suitable drug or combination of drugs for treating a predetermined condition. Preferably, the drug includes a drug for treating conditions such as glaucoma or allergies or a drug for delivering steroids or antibiotics.

As shown in FIG. 14, the mass 74 that forms the lacrimal filler 72 includes a drug or combination of drugs that are incorporated therein. Preferably, the mass 74 includes hyaluronic acid gels that include one or more drugs in their gel matrix. The hyaluronic acid is impregnated or embedded with the drug or drugs for slow, steady release upon dissolution of the hyaluronic acid.

Referring now to FIG. 15, there is schematically illustrated another embodiment of the lacrimal filler generally designated by the numeral 76. Unlike the embodiments shown in FIGS. 6-14, the lacrimal filler 76 shown in FIG. 15 includes an outer surface 78 that dissolves at a predetermined rate to release a drug and an inner core 80 for holding the drug.

Similar to the lacrimal filler 72 shown in FIG. 14, the lacrimal filler 76 shown in FIG. 15 includes any suitable drug or combination of drugs for treating a predetermined condition. The lacrimal filler outer surface 78 includes a material that dissolves at a predetermined rate to control the release of the drug. Preferably, the material is hyaluronic acid and the rate of dissolution is slow, so that the dissolution of the hyaluronic acid surface releases a steady amount of the drug onto the eyeball 32 shown in FIG. 1.

Figure 16:
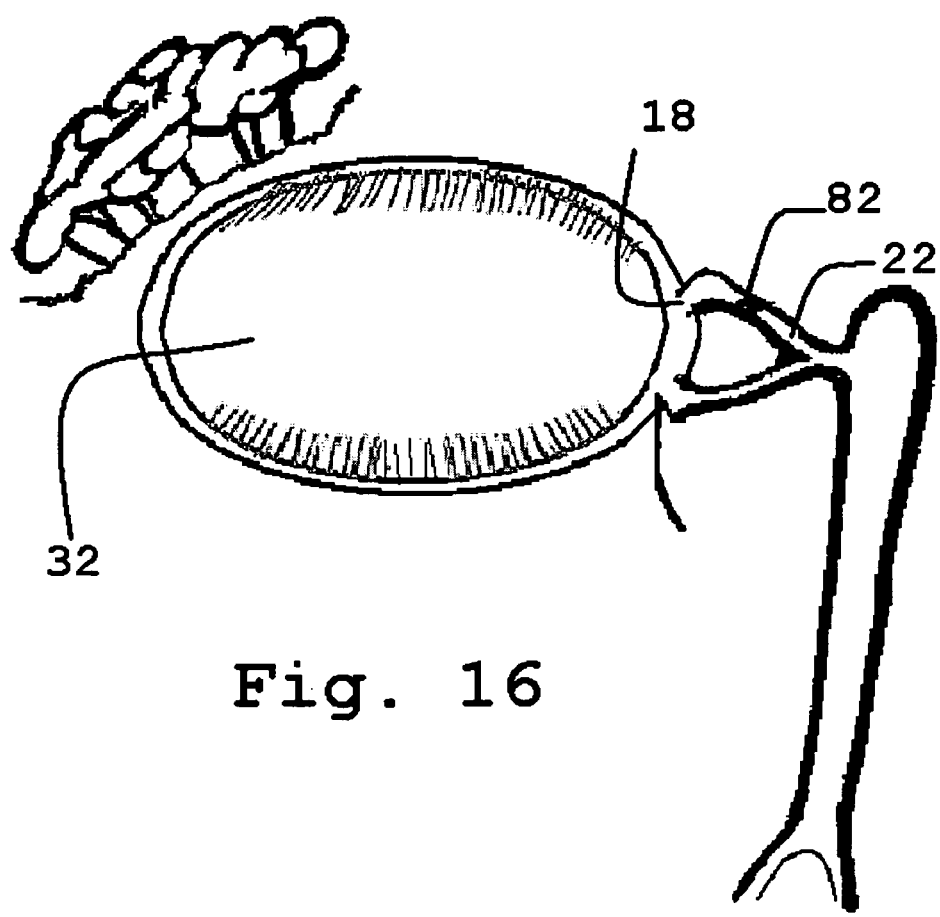
FIG. 16 is an enlarged fragmentary view in side elevation of another embodiment of a lacrimal filler within an upper canaliculus of the lacrimal outflow system.

Referring now to FIG. 16, there is shown another embodiment of a lacrimal filler generally designated by the numeral 82. Unlike the embodiment shown in FIGS. 6-13, the lacrimal filler 82 is formed from a mass (not shown) that is inserted through the punctum 18 and into the canaliculus 22.

The mass that forms the lacrimal filler 82 is essentially identical to the mass 50 shown in FIGS. 6-13. As a result, the only difference between the lacrimal filler 48 shown in FIGS. 6-13 and the lacrimal filler 82 shown in FIG. 15 is the placement of the lacrimal filler 82 in the canaliculus 22.

Figure 17:
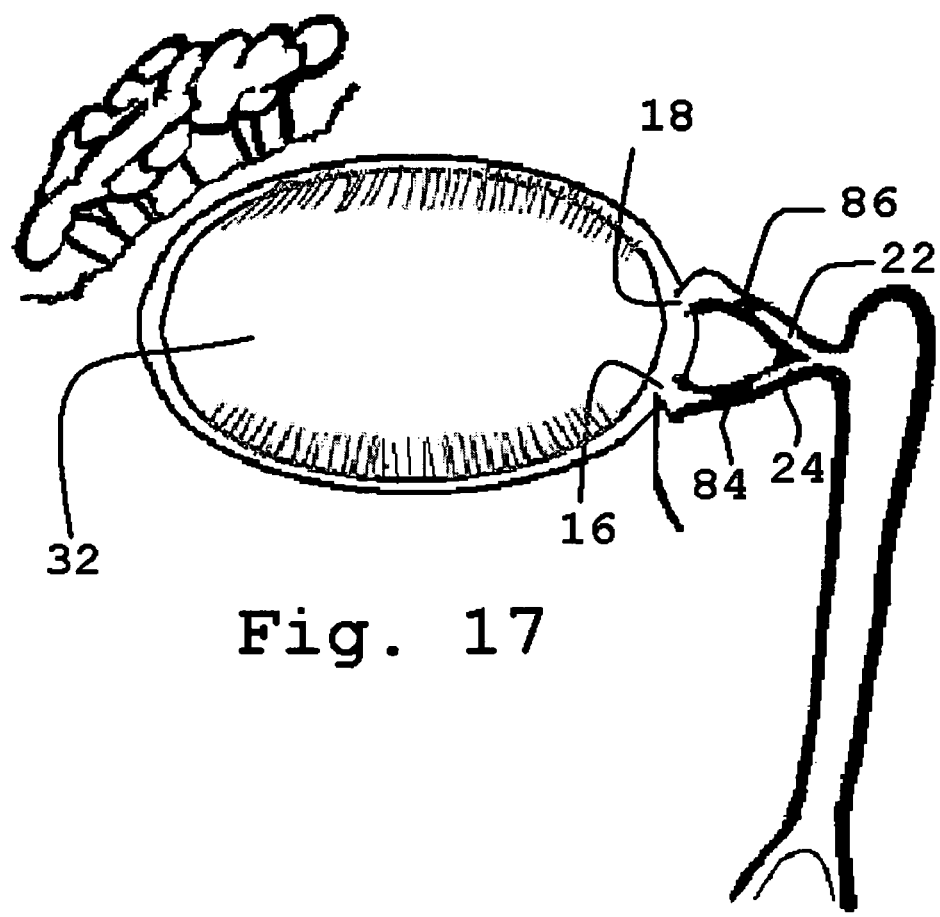
FIG. 17 is a view similar to FIG. 15 of another embodiment of a lacrimal filler within both the upper canaliculus and the lower canaliculus of the lacrimal outflow system.

Referring now to FIG. 17, there is shown an embodiment of the present invention that includes two lacrimal fillers generally designated by the numerals 84, 86. The lacrimal filler 84 is inserted through the punctum 16 into the canaliculus 24. The lacrimal filler 86 is inserted through the punctum 18 into the canaliculus 22.

The lacrimal filler 84 is essentially identical to the lacrimal filler 48 shown in FIGS. 6-13. The lacrimal filler 86 is essentially identical to the lacrimal filler 82 shown in FIG. 15. Preferably, the lacrimal fillers 84, 86 are delivered in the same syringe.

It should be understood that an embodiment for a kit for treating dry eye syndrome using the syringe and hyaluronic acid mass described above includes an enzyme for dissolving the hyaluronic mass, a hyaluronic acid mass that includes a drug delivery system, or both.

According to the provisions of the patent statutes, I have explained the principle, preferred construction and mode of operation of my invention and have illustrated and described what I now consider to represent its best embodiments. However, should be understood that, within the scope of the appended claims, the invention may be practiced otherwise than as specifically illustrated and described.

What is claimed is:

1. A kit for treating dry eyes comprising:
   a syringe,
   a lacrimal injector,
   a biomaterial mass comprising a swellable preformed hyaluronic acid gel occluder in a gel form, the hyaluronic acid being present in a concentration of between 15 mg/ml and 25 mg/ml,
   said lacrimal injector configured to inject said biomaterial mass into a canaliculus in the lacrimal outflow system to absorb liquid within the canaliculus and swell to conform the outer surface of the mass to the inner surface of the canaliculus to form a sealing mechanism for sealing the canaliculus at least partially,
   said sealing mechanism outer surface being sufficiently soft relative to the inner surface of the canaliculus to prevent the sealing mechanism outer surface from eroding the canaliculus lining, and
   said sealing mechanism forming an occlusion to prevent the outflow of liquid through the lacrimal outflow system to retain tears within the eye to maintain eye lubrication and wetness.

2. The kit as set forth in claim 1 which includes:
   said biomaterial mass having hyaluronic acid in a form selected from the group consisting of hyaluronic acid crystals, hyaluronic acid crystals suspended in hyaluronic acid liquid, hyaluronic acid gel, hyaluronic acid gel particles with hyaluronic acid solid particles, and hyaluronic acid solid particles.

3. The kit as set forth in claim 1 wherein:
   said biomaterial mass being suspended in a solution having a hyaluronic acid concentration of about 22 mg/ml.

4. The kit as set forth in claim 1, wherein:
   said hyaluronic acid is cross-linked.

5. The kit as set forth in claim 4 wherein:
   said hyaluronic acid having a degree of crosslinking ranging from 10% to 100% crosslinking.

6. The kit as set forth in claim 5 wherein:
   said hyaluronic acid having a degree of crosslinking ranging from 60% to 95% crosslinking.

7. The kit as set forth in claim 1 which includes:
   a punctal dilator for dilating the puncta to facilitate insertion of said syringe therein.

8. The kit as set forth in claim 1 which includes:
   an enzyme for dissolving said sealing mechanism.

9. The kit as set forth in claim 8 which includes:
   said enzyme being hyaluronidase.

10. The kit as set forth in claim 1 in which:
    said sealing mechanism includes a drug for treating a condition.

11. The kit as set forth in claim 10 in which:
    said sealing mechanism has an outer surface that dissolves at a predetermined rate to deliver said drug.

12. The kit as set forth in claim 11 in which:
    said drug includes a drug selected from the group consisting of a drug for treating glaucoma, a drug for treating allergies, steroids, and antibiotics.

13. The kit as set forth in claim 1, wherein the biomaterial mass is housed within the syringe, the hyaluronic acid having a volume of from 0.1 cc to 1 cc.

14. A method for treating dry eye, comprising the steps of:
    inserting an injector through a puncta and into a canaliculus in a lacrimal outflow system;
    inserting a swellable preformed hyaluronic acid gel occluder in a non-liquid gel form from the injector and into the canaliculus, such that the gel absorbs liquid in the canaliculus and swells to conform to the interior of and form a soft seal within the canaliculus, thereby preventing the outflow of liquid through the lacrimal outflow system with the occluder to retain tears within the eye to maintain eye lubrication and wetness
    wherein the occluder is suspended in a solution having a hyaluronic acid concentration of between 15 mg/ml and 25 mg/ml.

15. A method as set forth in claim 14, wherein the hyaluronic acid is cross-linked.

16. A method as set forth in claim 14, further including inserting a puncta dilator into the puncta, and dilating the puncta to facilitate insertion of a syringe and a catheter into the canaliculus prior to inserting the injector through the puncta and into the canaliculus.

* * * * *